United States Patent [19]

Klinger et al.

[11] Patent Number: 5,693,783
[45] Date of Patent: Dec. 2, 1997

[54] DNA PROBES FOR DETECTING THE MOST COMMON LIVEBORN CHROMOSOMAL ANEUPLOIDIES

[75] Inventors: Katherine Klinger, Framingham; William Dackowski, Hopkinton; Greg Landes, Northborough, all of Mass.

[73] Assignee: Genzyme Corporation, Cambridge, Mass.

[21] Appl. No.: 499,879

[22] Filed: Jul. 10, 1995

Related U.S. Application Data

[63] Continuation of Ser. No. 144,100, Oct. 27, 1993, abandoned, which is a continuation of Ser. No. 865,601, Apr. 9, 1992, abandoned.

[51] Int. Cl.$^6$ ................................................. C07H 21/04
[52] U.S. Cl. ...................... 536/24.31; 536/24.3; 536/23.1
[58] Field of Search .............................. 536/23.1, 24.3, 536/24.31, 24.32; 435/6, 810

[56] References Cited

U.S. PATENT DOCUMENTS

| | | | |
|---|---|---|---|
| 5,427,932 | 6/1995 | Weier et al. | 435/91.2 |
| 5,447,841 | 9/1995 | Gray et al. | 435/6 |
| 5,447,842 | 9/1995 | Simons | 435/6 |

FOREIGN PATENT DOCUMENTS

| | | | |
|---|---|---|---|
| 1301805 | 5/1992 | Canada | C12Q 1/68 |
| 0500290 | 8/1992 | European Pat. Off. | C12Q 1/68 |
| WO9009452 | 8/1990 | WIPO | C12Q 1/02 |
| WO9321342 | 10/1993 | WIPO | C12Q 1/68 |
| WO9403638 | 2/1994 | WIPO | C12Q 1/68 |

OTHER PUBLICATIONS

Klinger et al. (1991) Cytogenet. Cell Genet. vol. 58, p. 2148.
Klinger et al. (1991) Cytogenet. Cell Genet. vol. 58, p. 2149.
Cremer et al. (1988) Experimental Cell Research 176:199–220.
Cremer et al. (1982) Hum. Genet. 60:46–56.
Kuo et al. (1991) Am. J. Hum. Genet. 49:112–119.
Collins et al. (1991) Genomics 11:997–1006.
Lapidot–Lifson et al. (1996) Am. J. Obstet. Gynecol. 174:886–890.
Bryndorf et al. (1992) British Medical J. 304:1536–9.
Lichter et al. (1988) Proc. Natl. Acad. Sci. USA 85:9664–8.
Lichter et al. (1988) Hum. Genet. 80:224–234.
Julien et al. (1986) Lancet 11:862–864 (Oct. 11).
Ward et al. (Nov. 1992) Am. J. Hum. Genet. 51:A265, abstract 1047.
Prashad et al. (Nov. 1992) Am. J. Hum. Genet. 51:A262, abstract 1034.
Pinkel et al. (1988) Proc. Natl. Acad. Sci. USA 85:9138–42.
Lichter et al. (1990) Science 247:64–69.
Klinger et al. (1992) Am. J. Hum. Genet. 51:55–65.
Ward et al. (1993) Am. J. Hum. Genet. 52:854–865.
Griffin (1994) Int. Rev. Cytology 153:1–37.
Ried et al. (1992) Hum. Mol. Genet. 1:307–313.
Lebo et al. (Jul. 1992) Am. J. Med. Genet. 43:848–54.

*Primary Examiner*—Carla J. Myers
*Assistant Examiner*—Amy Atzel

[57] ABSTRACT

Single stranded nucleic acid molecules, which can be used as probes to detect human chromosomes 13, 18, 21, X and Y are described. These probes are useful alone or in combination for diagnosing aneuploidies of the five chromosomes which comprise 95% of liveborn chromosomal aneuploidies.

6 Claims, No Drawings

DNA PROBES FOR DETECTING THE MOST COMMON LIVEBORN CHROMOSOMAL ANEUPLOIDIES This application is a continuation of application Ser. No. 08/144,100 filed on Oct. 27, 1993, now abandoned; which is a continuation of Ser. No. 07/865,601 filed Apr. 9, 1992, now abandoned.

GOVERNMENT SUPPORT

The invention described herein resulted from studies which were supported in part by a grant from the National Institute of Health. The U.S. Government therefore has certain rights in the invention.

BACKGROUND

In situ hybridization has been a major research tool for molecular geneticists to visualize specific DNA or RNA sequences present in chromosomes, cells or tissues. Originally performed in an isotopic format, non-isotopic techniques, such as fluorescence in situ hybridization (FISH), are rapidly becoming the method of choice, because they can be accomplished faster, multiple signals can be detected at one time and hybridization signals can be more precisely localized. In general, however, non-isotopic methods have suffered from a lack of sensitivity. In addition, although simultaneous use of multiple fluors has been proposed in theory, in fact only one or two color FISH has been common to date.

Because conventional prenatal cytogenetic analysis for chromosomal abnormalities requires 1 to 3 weeks, there has been great interest in applying FISH to prenatal diagnosis. Previous studies have demonstrated the general feasibility of detecting chromosomal abnormalities in interphase nuclei by fluorescence in situ hybridization (Cremer, T., et. al., Hum. Genet. 60:46–56 (1982); Julien, C., et. al., Lancet ii: 862–864 (1986); Lichter, P., Proc. Natl. Acad. Sci. USA: 85:9664–9668 (1988); Pinkel, D., Proc. Natl. Acad. Sci. USA: 85:9138–9142 (1988);); Lichter, P., Science 247:64–69 (1990)).

However, the probes used in these studies achieved limited hybridization efficiency due in part to constraints of probe composition, as well as variations in sample preparation and hybridization detection. In practice this meant that many chromosomes did not hybridize, and that of those nuclei that did hybridize, many had fewer hybridization signals than expected. For example, complex probes composed of the inserts from an entire chromosome library (e.g. as described in Pinkel, D., Proc. Natl. Acad. Sci. USA: 85:9138–9142 (1988), Lichter, P., et. al., Hum. Genet. 80:224–234 (1988); Cremer, C. P., et. al., Hum. Genet. 80:235–246 (1988); and Jauch, A., et. al., Hum. Genet. 85:145–150 (1990)) generate a very large diffuse signal, such that the edges of the signal can be difficult to delineate, and overlap of the hybridization domains is common.

On the other hand, alpha satellite repeat probes (e.g. as described in Willard, H. F. and J. S. Waye Trends Genet. 3:192–198 (1987)), which hybridize to repeated sequences localized around the chromosome centromere, generate a brilliant hybridization signal, but present some difficulties in clinical utilization. In general, chromosome specificity of the repetitive probes is very sensitive to hybridization conditions, and the signal size is sensitive to pericentromeric heteromorphisms. In addition, the alpha satellite repetitive elements present on chromosomes 21 and 13 are the same and thus can not be differentiated using the alpha satellite repeat probes. Furthermore, the centromeric position of the probes does not allow identification of all manifestations of Down's Syndrome (i.e. Robertsonian translocations).

Composite probe sets composed of single copy subclones (i.e. plasmid pools) (e.g. as described in Lichter, P., et. al., Proc. Natl. Acad. Sci. USA 85:9664–9668 (1988)), have given good signal resolution and specificity, but the signal is often comprised of many smaller signals, which complicates the quantitation (Lichter, P. et. al., "Detection of Down Syndrome by In Situ Hybridization With Chromosome 21 Specific DNA Probes" in D. Patterson, ed. Molecular Genetics of Chromosome 21 and Down Syndrome, Wiley-Liss, Inc., New York (1990)).

The most common chromosomal abnormalities in newborns are trisomy 21, (Down's Syndrome) with an incidence of 1/800, trisomy 18 (Edward Syndrome), with an incidence of 1/8000, trisomy 13 (Patau Syndrome), with an incidence or 1/20,000, monosomy X (Turner's Syndrome), with an incidence of 1/10,000 and other sex chromosome aneuploidies, such as Kleinfelter Syndrome (XXY), with a combined incidence of 1/1000 (Thompson, J. S. and M. W. Thompson eds. Genetics in Medicine, W. B. Saunders Co., Philadelphia, Pa. (1986)). Together aneuploidies of these 5 chromosomes account for 95% of liveborn chromosome abnormalities, which are accompanied by birth defects in the child (Whiteman, D. A. H. and K. Klinger, Intl. Congress Hum. Genet. (in Press)).

Methods which allow rapid and accurate detection of the major fetal aneuploidies would be valuable, since they would provide prospective parents and medical practitioners with additional time to consider the test results and develop a thoughtful course of action.

SUMMARY OF THE INVENTION

The invention relates to single-stranded nucleic acid molecules (DNA or RNA) which are capable of specifically hybridizing to portions of human chromosomes 13, 18, 21, X and Y. The nucleic acid molecules specific for chromosome 13 comprises cosmid contigs, which is capable of hybridizing to 65–100 kbs of nonoverlapping DNA at human chromosomal locus 13q13 (D13S6). The molecules specific for chromosome 18 comprises cosmid contigs, which are capable of hybridizing to 65–110 kbs of nonoverlapping DNA at human chromosomal locus 18q22-qter. The nucleic acid molecules for chromosome 21 comprises cosmid contigs, which are capable of hybridizing to 65–100 kbs of nonoverlapping DNA in human chromosomal locus 21q22.3 (D21S71). The molecule capable of hybridizing to the X chromosome is a single cosmid that contains a repeat sequence that hybridizes around the centromere and the Y probe is pDP97, a repetitive repeat clone.

The invention also relates to nucleic acid probes labelled with a detectable marker, that can be prepared from such molecules or fragments thereof. Each of the five probes specifically hybridizes to a unique locus on either chromosome 13, 18, 21, X or Y, producing a high signal-to-noise ratio and exhibiting a high hybridization/detection efficiency. These probes are therefore useful diagnostically.

The invention further relates to methods of using the probes and kits comprising the probes, each alone or in combination to detect chromosomes 13, 18, 21, X and Y and to diagnose chromosomal aneuploidies. For example, the probes can be used for prenatal analysis. The chromosome 21 specific probe can be used to diagnose trisomy 21, (Down's Syndrome), including trisomy 21 due to a Robertsonian translocation; the chromosome 18 specific probe can be used to diagnose trisomy 18, (Edward Syndrome); the chromosome 13 specific probe to diagnose trisomy 13 (Patau Syndrome); and the X and Y probes to diagnose monosomy X (Turner's Syndrome), Kleinfelter Syndrome (XXY) and other sex chromosome aneuploidies.

The probes of the subject invention generate bright, easily detected hybridization signals which are spatially well-resolved when hybridized to human chromosomes 21, 18, 13, X and Y. In addition, the probes have consistently exhibited hybridization efficiencies of about 95%. Further, the same hybridization conditions yield equivalent performance characteristics for all five probes, allowing them to be used simultaneously.

Use of the probes disclosed herein in hybridization assays yields accurate results, which can be accomplished in a much shorter amount of time (i.e. less than 24 hours) than the time required to perform cytogenetic analysis (i.e. approximately 7 days, with turnaround times of greater than two weeks being common). Therefore, in situ analysis using the probes disclosed herein provides prospective parents and medical practitioners with additional time to consider the test results and to develop a thoughtful course of action.

DETAILED DESCRIPTION OF THE INVENTION

The invention is predicated on the development of nucleic acid molecules which are capable of specifically hybridizing to portions of human chromosomes 13, 18, 21, X and Y. These molecules or fragments thereof can be labelled to form probes, which can then be hybridized in situ to detect those specific subregions of the respective human chromosomes. Although the invention is specifically described with respect to the use of DNA molecules as probes, one of ordinary skill in the art would understand that a ribonucleic acid (RNA) molecule could also be used as a hybridization probe. Methods for preparing such RNA molecules are known in the art.

The DNA molecules, which hybridize to chromosomes 13, 18, 21, X and Y were deposited with the American Type Culture Collection on Mar. 19, 1992, and have been assigned ATCC Accession Numbers 68936, 68934, 68935, 68932, and 68933, respectively.

The DNA molecules specific for chromosomes 13, 18 and 21 were generated by screening a human chromosome library with single copy clones mapping to human chromosomal loci 13q13 (D13S6), 18q22-qter (myelin basic protein, MBP) and 21q22.3 (D21S71, the region implicated in Down's Syndrome), respectively to identify cosmids (i.e. clones having an insert size of 33–52 kb). These primary cosmids were then used in chromosome walking to obtain cosmids whose inserts minimally overlap with that of the primary cosmid. Several rounds of chromosome walking were performed in a unidirectional manner from the secondary cosmids until the contiguous chromosomal segment within the set of cosmids, or cosmid contigs, totalled greater than 100 kb. The contigs were rigorously characterized to obtain the molecules of the subject invention. The DNA molecules specific for chromosome 21, 13 and 18 comprise a pool of three cosmids each, while the DNA molecule specific for the X chromosome is one cosmid.

Deoxyribonucleic acid (DNA) probes, labelled with a detectable marker can be prepared from cloned DNA molecules or fragments thereof according to procedures which are well known in the art. Such techniques include incorporation of radioactive labels, direct attachment of fluorochromes or enzymes, and various chemical modifications of the nucleic acid fragments that render them detectable immunochemically or by other affinity reactions. A preferred method of labelling is by nick translation using a haptenated nucleoside triphosphate (e.g. biotin labelled dUTP) or by random primer extension (Feinberg & Vogelstein, *Anal. Biochem.* 137:266–267, 1984) (e.g. multiprime DNA labeling system (Amersham)) substituting dTTP with Bio-11-dUTP. (Langer, P. R., et. al., *Proc. Natl. Acad. Sci. USA,* 78:6633–37 (1981); Brigati, D. J., et. al., *Virology,* 126:32–50 (1983)). Once labelled, the probes of the subject invention can be applied to chromosomes using standard in situ hybridization techniques.

For maximum clinical utility, it is important that probes be chromosome-specific, and that they are of a complexity, which is optimized for both signal-to-noise ratio and for spatial resolution of the hybridization signal. The chromosome 18, 18, 21, X and Y probes of the subject invention were tested for hybridization efficiency and specificity against both metaphase spreads and interphase nuclei using short-term blood cultures and uncultured amniotic samples, respectively, as detailed in Example 1.

The presently described locus-specific probes generate bright, easily detected hybridization signals which are spatially well-resolved, when hybridized under suppression conditions to human metaphase spreads of chromosome 21, human chromosome 18, human chromosome 13, human chromosome X and human chromosome Y. The estimated hybridization efficiency when the probes are hybridized to the metaphase spreads according to the method disclosed in Example 1, is around 95%. Over 500 clinical amniotic fluid samples were also analyzed using the probes and sample processing protocols optimized for uncultured amniocytes. Greater than 95% of the nuclei tested with these probes were found to be scorable and over 90% of the nuclei sampled exhibited the correct number of hybridization signals.

In addition to being used separately, each of the five probes can be distinctly labelled in such a manner that they can be used in combination to simultaneously detect more than one aneuploidy. Three sets of distinguishable fluorophores, emitting in the green (fluoroscein), in the red (rhodamine or Texas Red), and in the blue (AMCA or Cascade Blue) are typically used for FISH. Therefore, by using standard procedures, at least three of the probes can be used in combination to simultaneously detect three chromosomal aneuploidies. In addition, all five probes can be simultaneously visualized by methods disclosed in Example 1 (See also Ried et. al. *Proc. Natl. Acad. Sci. USA,* 89:1388–1392, 1992).

Methods for performing in situ hybridization are well-known in the art. In general, a cell sample is deposited or placed onto a slide, rendered available for hybridization, contacted with the probe, and allowed to hybridize. Detection of hybridization is indicative of the presence in the sample of a sequence complementary to the probe. The probes of the subject invention hybridize to regions of chromosomes 13, 18, 21, X and Y, which are involved in aneuploidies. Therefore, the probes can be used diagnostically, for example in fetal screening of cells isolated inter alia from amniotic fluid withdrawn from the womb, from chorionic villus tissue, from fetal cells isolated from maternal blood (e.g. by flow sorting) or from cervical secretions.

The chromosome 21 specific probe can be used to diagnose trisomy 21 (Down's Syndrome). The non-centromeric localization of the probe also allows detection of trisomy 21 due to Robertsonian translocation. The chromosome 18 specific probe is useful for diagnosing trisomy 18, (Edward Syndrome); the chromosome 13 specific probe set for diagnosing trisomy 13 (Patau Syndrome); and the X and Y probe sets for diagnosing monosomy X (Turner's Syndrome) and other sex chromosome aneuploidies, such as Kleinfelter Syndrome (XXY). The same hybridization conditions yield equivalent performance characteristics for all five probes, allowing them to be used for multicolor analysis when combined with multicolor fluorescence, A kit comprising the probes of the subject invention, which can be used for detecting chromosomes 21, 18, 13, X and Y and for diagnosing chromosomal aneuploides, can be produced. It includes, for example, a container for holding the required components, solutions for fixing (settling) nuclei to slides, probes, solutions to stain hybridized probes, and slides, which can be silanized to better hold nuclei. In a preferred embodiment the probe(s) comprise a cocktail consisting of competitor DNA (for suppression hybridization).

Cytogenetic analysis, which generally consists of cytogenetic banding of metaphase chromosomes, is now routinely offered to women at risk of having a child with a chromosomal abnormality, the most common indications being advanced maternal age, abnormal maternal serum alphafetoprotein (MSAFP), abnormal combined levels of MSAFP, bHCG and estriol, or family history. Currently used cytogenetic assays are accurate, and often detect quite subtle rearrangements. However, even though advances in culture methods and staining techniques have decreased the time required to carry out an analysis, under the best circumstances, it takes approximately 7 days to complete a test, and turn around times of greater than two weeks are common. The probes disclosed herein can be used to rapidly analyze chromosomes in situ, allowing identification of trisomic chromosome constitution in significantly less time.

The present invention will now be further illustrated by the following examples, which are not intended to be limiting in any way.

Example 1: Rapid Detection of Aneuploidies in Interphase Nuclei Obtained from Uncultured Amniocytes and Metaphase Spreads Prepared From Short-term Blood Cultures Using Probes to Chromosomes 21, 18, 13, X and Y Nuclei Preparation The chromosome 21, 18, 13, X and Y probes were evaluated by FISH against both metaphase spreads and interphase nuclei using short-term blood cultures and uncultured amniotic samples, respectively. Metaphase spreads were prepared from short-term blood cultures and fixed to slides using standard cytogenetic protocols.

Special techniques are required for fixing or settling a sample of fetal cells isolated from amniotic fluid, because in addition to informative cells, such a sample generally includes many dead and dying cells.

The following solutions were prepared:
PBS:
32 g NaCl, 0.8 g KCl and 8.68 g $NaH_2PO_4 7H_2O$. Make up to 4 liters with distilled $H_2O$, pH to 7.5.
Carnoy's Fixative:
75 ml methanol
25 ml glacial acetic acid
0.075M KCl:
Dissolve 5.59 g KCl in 1 liter distilled $H_2O$. Filter sterilize using 0.2 micron filter flask.:

30% Fix in 0.075M KCl:
3 ml Carnoy's Fixative
7 ml KCl
2% solution of 3-Aminopropyltriethoxysilane:
5 ml of 3-Aminopropyltriethoxysilane
250 ml acetone Clean glass microscope slides were placed in a slide rack and submerged for 2 minutes in the 2% solution described above. The slides were removed from the solution after the 2 minute submersion period and rinsed in two changes of distilled water. The slides were drained and allowed to air dry. Prepared slides were stored in a dust free box at room temperature.

An amniotic fluid sample was spun in a centrifuge tube at 2100 RPM (1029 G) for 7 minutes at room temperature. The supernate was removed by aspiration. The pellet was resuspended in 50 ul of PBS per 1 ml of original fluid volume. 25 ul of resuspended pellet in PBS was placed on a silanized glass microscope slide. If a substantial amount of blood was present in the amniotic fluid, 1 drop of 30% 3:1 methanol:glacial acetic acid fixative (Carnoy's fixative) in 70% 0.075M KCl was added.

Slides were placed horizontally in a humid chamber at a temperature of 37 degree C. for 15 minutes. This incubation period allows informative cells to settle onto the surface of the silanized slide surface undisturbed while dead cells, or other cells having damaged membranes, remain floating in the buffer. After 15 minutes, 50 ul of 0.075 KCl hypotonic solution (prewarmed to 37 degrees C.) was gently added to the buffered solution containing the resuspended cell pellet followed by an additional 15 minutes incubation in the heated humid chamber. The hypotonic solution causes the viable cells to swell, making it easier to remove cytoplasm and cell membrane in subsequent steps.

After the 15 minute incubation in KCl at 37 degrees C., the fluid was gently tipped from each slide (to the side, not lengthwise). The slides were not allowed to dry at this step. As each slide was tipped off, it was placed flat on a paper towel and 100 ul of 30% Carnoy's fixative in 70% 0.075M KCl was gently added. The slides were left undisturbed in this condition for a period of 5 minutes. The 30% fix/KCl ruptures the swollen cell membranes and conditions the cells to the fix.

After the 5 minute incubation, fluid was gently tipped from each slide. The slides were not allowed to dry out. 5–6 drops of fresh undiluted Carnoy's fixative was immediately dropped onto the region of the slide containing the fetal cells. The slides were incubated for approximately 5 minutes, then transferred to a 60 degree C. slide warmer and allowed to dry. This fixative treatment ruptures any remaining membranes and rinses away residual debris while fixing the nuclei to the slide.

Following this fix step, excess fluid is removed by tipping the slide and the slides are placed on a slide warmer to dry. When the slides are dried they are processed through an ethanol series prior to hybridization. In coplin jars, the slides are contacted sequentially with 70%, 80%, 90% and 100% ethanol for 1 minute in each dilution. The slides are then allowed to dry at room temperature.

Probe Labelling

The five chromosome-specific probe set was labeled by nick translation as follows: The chromosome 21 probe was labeled with DNP-dUTP; the chromosome 18 probe with biotin-dUTP; the chromosome 13 probe with digoxigenin-dUTP; the chromosome X probe with biotin-dUTP and digoxigenin-dUTP; and the Y-probe, pDP97 with both digoxigenin-dUTP and DNP-dUTP.

Hybridization

Hybridization was performed on the slides under suppression conditions, basically as described by Lichter et. al. (Cremer, T., et. al. *Hum. Genet.* 80:235–246 (1988); Lichter, P., et. al., *Hum. Genet.* 80:224–234 (1988)). The concentration of probes used was 5, 2.5 and 1 µg/ml for each autosomal cosmid contig, chromosome X-specific cosmid and chromosome Y repeat, rspectively, Hybridizations were performed in 10 µl of hybridization cocktail containing 6xSSC (1xSSC=0.15M NaCl and 0.015M sodium citrate, pH 7), 10% (W/V) dextran sulfate, 50% (V/V) formamide, 100 µg/ml sonicated human DNA (except for chromosome Y repeat) and 900 µg/ml sonicated salmon DNA. In a small number of samples, human COT 1 DNA (200 µg/ml; GIBCO BRL, Life Technologies, Inc., Gaithersburg, Md.) was used instead of total human DNA. Probe and target DNA were denuated simultaneously under a sealed coverslip for 8 minutes at 80° C. Following hybridization overnight at 37° C., slides were washed three times for five minutes each in 50% formamide/2XSSC (1XSSC=0.15M NaCl and 0.15M sodium citrate, pH 7) at 42° C., then three times for five minutes each in 0.1XSSC at 60° C. Slides were incubated with avidin-FITC (5 µg/ml) in 4xSSC/1% BSA/0.1% Tween 20 at 37° C. for 30 minutes in a moist chamber. Slides were then washed 3 times with 4xSSC/0.1% Tween 20 for 5 minutes at 42° C.

Detection

Detection was carried out as described by Lichter et. al. (Cremer, T., et. al. *Hum. Genet.* 80:235–246 (1988); Lichter, P., et. al., *Hum. Genet.* 80:224–234 (1988). Biotinylated probes were detected with either avidin-FITC or avidin-Texas Red (Vector Laboratories, Burlingame, Calif.). Digoxigenin-labeled probes were detected with antidigoxigenein-FITC (Boehringer Manneheim, Indianapolis, Ind.). No signal amplification was used in these studies. All studies comparing probe performance were performed as single probe hybridizations using biotinylated probes detected with avidin-FITC. In some experiments, simultaneous hybridization and detection of the X (digoxigenin/antidigoxigenin-FITC) and the Y (biotin/avidin Texas Red) probes was carried out.

The slides were mounted in 2.33% DABCO antifade (D2522, Sigma Chemical Co., St. Louis, Mo.) in 100 mM Tris, pH 8.0, 90% (V/V) glycerol prior to analysis, and were occassionally counterstained with 4';6-diamidino-2-phenylindole (DAPI) or propidium iodide. At other times, less stringent suppression conditions were used to allow repetitive DNA to hybridize, permitting visualization of the nucleus without counterstain. All results were visualized using a Zeiss Axioplan epifluorescence microscope. A dual band pass filter (Omega Optical Inc., Brattleboro, Vt.) was used to visualize the FITC and Texas Red simultaneously. Results were photographed directly from the microscope using a 35 mm camera and Kodak Gold 400 film.

Example 2: Comparison of Results Obtained Using In Situ Hybridization and the Probes Described Herein with Results Obtained Using Standard Cytogenetic Analysis To compare interphase cytogenetics with conventional cytogenetics, samples of amniotic fluid (generally 1.5–5 ml.) were obtained from collaborating clinical laboratories and identified only by patient identification numbers. A standard cytogenetic analysis was carried out on each sample by the collaborating laboratory. Upon receipt, the samples were further encoded by assignment of an internal ID number. The latter was the only identifier available to the investigators. Thus evaluation of probe was carried out in a blind manner. No cell culture was performed prior to in situ hybridization. A minimum of 50 hybridized nuclei (50–1296) were counted per probe for each sample, and the number of nuclei displaying 1,2,3 or 4 hybridization signals recorded. Overlapping or clumped cells were not counted. Each signal visualized was counted as one signal for the purposes of statistical analysis, even if they were part of the closely spaced paired signals characteric of a G2 nucleus. Samples were then decoded and categorized as normal or abnormal as determined by the karyotype analysis.

When the hybridization analysis of the uncultured amniotic fluid samples was complete, data were analyzed in the following manner: first, the percent of total nuclei counted which displayed 0,1,2,3 or 4 signals was calculated. Samples were categorized as normal or abnormal based on karyotype. These results were compared to those obtained by interphase cytogenetics, which revealed that each of the autosomal probe sets have approximately equivalent performance characteristics, and that efficient hybridization/detection was achieved. When the results from 915 analyses were pooled, on average, approximately 90% of the hybridized nuclei in any given disomic sample displayed two signals when analyzed using one of the autosomal probe sets. Only 11 samples displayed less than 70% two signal nuclei, and in all disomic samples at least 50% of the hybridized nuclei displayed two signals. Interphase cytogenetics accurately identified all samples as disomic for these autosomes. Few disomic nuclei displayed three hybridization signals (x21= 4%, x18=3%, x3%). Similar results were obtained for the sex chromosomes, where XX and XY genotypes were distinguished.

Twenty one samples of abnormal karyotype were analyzed in the course of the study. Trisomy 21 represented 14 of the 21 samples; there were 2 cases each of trisomy 18 and 13, and three sex chromosome aneuploidies (1 XX/XXX, 2XXY). Trisomic samples were clearly discriminated from normal samples. The frequency of trisomic cells displaying three hybridization signals ranged from 45 to 88%, with the exception of one sample with substantial maternal contamination due to the presence of maternal blood. In this data set, there was no overlap between the percent of three signal nuclei in normal samples and the percent of three signal nuclei in trisomic samples. Normal and abnormal genotypes were accurately assigned to all samples. This included one case of trisomy 21 caused by a 21:21 Robertsonian translocation (88% of hybridized nuclei displayed three signals).

In this study, the hybridization pattern of all trisomic samples was clearly distinct from that seen in normal cells, demonstrating the sensitivity and specificity of interphase cytogenetics. However, reflecting the incidence of chromosomal abnormalities seen in cytogenetics, the number of aneuploid samples present in the series was small (n=21). Given that most samples in a clinical series will be normal, the power of the data set to discriminate between normal and aneuploid samples was addressed in order to generalize a protocol from these results to make prospective assignments of genotype. A statistical analysis showed that the data set supports the assignment of cutoff values such that samples in which fewer than 23% of the nuclei display three hybridization signals are predicted to be disomic for a given chromosome, samples in which 42% or greater of the nuclei exhibit three signals are predicted to be trisomic, and hybridization patterns that generate between 23 and 42% three signal nuclei are held to be indeterminate. Using these criteria, there was no overlap in the confidence intervals predictive of normal or abnormal status at either the 95% or 99% levels. The nonoverlapping distribution of signals obtained suggest that this technique has a direct clinical application as an indicator of the presence of trisomic cells.

Equivalents

Those skilled in the art will recognize or be able to ascertain using no more than routine experimentation, many equivalents to the specific embodiments of the invention described specifically herein. Such equivalents are intended to be encompassed in the scope of the following claims.

We claim:

1. Nucleic acid probe ATCC Accession No. 68936 that specifically hybridizes to about 65 kb to about 100 kb of a contiguous nucleotide sequence at chromosomal banding region 13q13 on chromosome 13.

2. Nucleic acid probe ATCC Accession No. 68934 that specifically hybridizes to about 65 kb to about 110 kb of a contiguous nucleotide sequence at chromosomal banding region 18q22-qter on chromosome 18.

3. Nucleic acid probe ATCC Accession No. 68935 that specifically hybridizes to about 65 kb to about 100 kb of a contiguous nucleotide sequence at chromosomal banding region 21q22.3 on chromosome 21.

4. Nucleic acid probe ATCC Accession No. 68932 that specifically hybridizes to a nucleotide sequence at the centromere region on the X chromosome.

5. A kit for detecting chromosomal aneuploidies, wherein the kit consists of:

a) nucleic acid that specifically hybridizes to about 65 kb to about 100 kb of a contiguous nucleotide sequence only at chromosomal banding region 13q13 on chromosome 13;

b) nucleic acid that specifically hybridizes to about 65 kb to about 110 kb of a contiguous nucleotide sequence only at chromosomal banding region 18q22-qter of chromosome 18;

c) nucleic acid that specifically hybridizes to about 65 kb to about 100 kb of a contiguous nucleotide sequence only at chromosomal banding region 21q22.3 of chromosome 21;

d) nucleic acid that specifically hybridizes to a nucleotide sequence only at the centromere region on the X chromosome;

e) nucleic acid that specifically hybridizes to a nucleotide sequence only at a chromosomal banding region on the Y chromosome;

f) fixing solution; and g) staining solution.

6. The kit according to claim 5, wherein said nucleic acids are selected from the group consisting of ATCC Accession Nos.: 68936, 68935, 68934, 68933 and 68932.

* * * * *